United States Patent
Natterer et al.

(10) Patent No.: US 6,631,285 B2
(45) Date of Patent: Oct. 7, 2003

(54) FAST TRANSFORM FOR RECONSTRUCTION OF ROTATING-SLAT DATA

(75) Inventors: Frank Natterer, Münster (DE); Frank T. Wübbeling, Münster (DE)

(73) Assignee: Koninklijke Philips Electronics, N. V., Eindhoven (NL)

( * ) Notice: Subject to any disclaimer, the term of this patent is extended or adjusted under 35 U.S.C. 154(b) by 202 days.

(21) Appl. No.: 09/808,931

(22) Filed: Mar. 15, 2001

(65) Prior Publication Data

US 2002/0177773 A1 Nov. 28, 2002

(51) Int. Cl.$^7$ .................................. A61B 6/00
(52) U.S. Cl. ................ 600/436; 600/407; 600/425; 600/431; 382/131; 250/363.1; 378/4; 378/901
(58) Field of Search .................. 378/4, 401; 600/407, 600/425, 436, 430; 250/363.1

(56) References Cited

U.S. PATENT DOCUMENTS

| | | | |
|---|---|---|---|
| 4,090,080 A | | 5/1978 | Tosswill .................. 250/366 |
| 4,262,207 A | | 4/1981 | Tosswill .................. 250/366 |
| 4,626,991 A | * | 12/1986 | Crawford et al. .............. 378/4 |
| 4,982,096 A | | 1/1991 | Fujii et al. .................. 250/367 |
| 5,077,770 A | | 12/1991 | Sammon .................. 378/101 |
| 5,967,983 A | | 10/1999 | Ashburn .................. 600/436 |
| 5,991,357 A | | 11/1999 | Marcovici et al. ............. 378/19 |
| 6,002,738 A | * | 12/1999 | Cabral et al. .................. 378/4 |
| 6,046,454 A | | 4/2000 | Lingren et al. ............. 250/370 |
| 6,055,450 A | | 4/2000 | Ashburn .................. 600/431 |
| 6,091,070 A | | 7/2000 | Lingren et al. ........ 250/370.09 |

OTHER PUBLICATIONS

Lodge et al. "A prototype rotating slat collimator for single photon emission computed tomography" IEEE Transactions on Medical Imaging, vol. 15(4):500–511, Aug. 1996.*

Zeng et al. "Image reconstruction algorithm for a rotating slat collimator" 2001 IEEE Nuclear Science Symposium Conference Record, PP. 1860–1873, San Diego, CA Nov. 4–10, 2001.*

(List continued on next page.)

*Primary Examiner*—Marvin M. Lateef
*Assistant Examiner*—Barry Pass
(74) *Attorney, Agent, or Firm*—Fay, Sharpe, Fagan, Minnich & McKee, LLP (57) ABSTRACT

A nuclear medical imaging apparatus receives an associated object (18). A radiation detector (12) is equipped with a slat collimator (14) including a plurality of spaced apart slats (114) separating individual detecting elements of an essentially linear array of detecting elements (116). The slat collimator produces planar collimation and results in projection data which is weighted inversely with distance in the projection direction. An image reconstruction processor (34) converts the projection data obtained by the detector (12) into an image, including correction for the inverse distance weighting. The image reconstruction processor (34) includes a memory, a preconditioning operator P (36), a projection operator S (38), and an iterative loop operator (40) which applies the preconditioning operator P (36) and the projection operator S (38) to the memory contents to calculate updated memory contents. The iterative loop operator (40) iteratively corrects for the inverse distance dependence of the projection data.

19 Claims, 5 Drawing Sheets

OTHER PUBLICATIONS

G.L. Zeng, et al. "Eigen Analysis of Cone–Beam Scanning Geometries". *Three–Dimensional Image Reconstruction in Radiation and Nuclear Medicine* © 1996 by Kluwer Academic Publishers, Netherlands. pp. 75–86.

G. L. Zeng, et al. "A cone beam tomography algorithm for orthogonal circle–and–line orbit". *Phys. Med. Biol.*, 1992, vol. 37, No 3, 563–577.

S. Webb, et al., "Monte Carlo modelling of the performance of a rotating slit–collimator for improved planar gamma–camara imaging," *Phys. Med. Biol.*, vol. 37, No. 5, 1095–1108, 1992.

Mauderli, et al., A Computerized Rotating Laminar Radionuclide Camera, *J. Nucl. Med*, 20:341–344 (1979).

Entine, et al., "Cadmium Telluride Gamma Camera," *IEEE Transactions on Nuclear Science*, vol. NS–26, No. 1:552–558 (1979).

Urie, et al., "Rotating Laminar Emission Camera with GE–detector," *Med. Phys.* 8(6) :865–870 (1981).

Mauderli, et al., "Rotating Laminar Emission Camera with GE–Detector: An Analysis," *Med. Phys.* 8(6):871–876 (1981).

Malm, et al., "A Germanium Laminar Emission Camera," *IEEE Transactions on Nuclear Science*, vol. NS–29, No. 1:465–468 (1982).

Mauderli, et al., "Rotating Laminar Emission Camera with GE–Detector: Further Developments," *Med. Phys.* 14(6) : 1027–1031 (1987).

* cited by examiner

FAST TRANSFORM FOR RECONSTRUCTION OF ROTATING-SLAT DATA

BACKGROUND OF THE INVENTION

The present invention relates to the art of diagnostic imaging. It finds particular application in conjunction with rotating one-dimensional (1D) slat-collimated gamma cameras and single photon emission computed tomography (SPECT), and will be described with particular reference thereto. However, it is to be appreciated that the present invention is also amenable to other like applications and other diagnostic imaging modes such as, e.g., positron emission tomography (PET).

In diagnostic nuclear imaging, one or more radiation detectors are mounted on a movable gantry to view an examination region which receives a subject therein. Typically, one or more radiopharmaceuticals or radioisotopes such as $^{99m}$Tc or $^{18}$F-Fluorodeoxyglucose (FDG) capable of generating emission radiation are introduced into the subject. The radioisotope preferably travels through a portion of the circulating system or accumulates in an organ of interest whose image is to be produced. The detectors scan the subject along a selected path or scanning trajectory and radiation events are detected on each detector.

In a traditional SPECT Anger camera, the detector includes a scintillation crystal that is viewed by an array of photomultiplier tubes. A collimator which includes a grid- or honeycomb-like array of radiation absorbent material is located between the scintillation crystal and the subject to limit the angle of acceptance of radiation which will be received by the scintillation crystal. The relative outputs of the photomultiplier tubes are processed and corrected to generate an output signal indicative of the position and energy of the detected radiation. A detector of this type isolates a scintillation event as originating along an approximate ray or line of view, or more precisely along a narrow-angle cone of view. Because radiation events along a spatial line are projected through an opening of the collimator array grid or honeycomb, the collected data is often referred to as projection data. The projection data is then reconstructed into a three-dimensional image of a region of interest by a reconstruction processor.

A rotating laminar emission camera, also known as the rotating laminar radionuclide camera, has linear collimators usually formed by mounting parallel collimating plates or slats between a line of individual detectors. Alternately, individual detector areas of a large-area detector are defined and isolated through the placement of slats. The slat collimator isolates planar spatial projections; whereas, the grid collimator of traditional scintillation detectors isolates essentially linear spatial projections. The detector-collimator assembly of a slat camera is typically rotated about an axis perpendicular to the detector face in order to resolve data for accurate two-dimensional image projection. Again, projection data collected at angular orientations around the subject are reconstructed into a three-dimensional volume image representation.

While maintaining certain advantages, such as a better sensitivity-resolution compromise, over, e.g., traditional Anger cameras, slat detectors are burdened by some other undesirable limitations. For example, the one dimensional collimation or slat geometry used by slat detectors complicates the image reconstruction process. The slat geometry results in a plane integral reconstruction as opposed to the line integral reconstruction that is generally encountered in traditional Anger camera applications. Moreover, the geometry produces a plane integral only in a first approximation.

In actuality, the plane integral should have a weighting factor introduced thereto to account for the fact that the detector's sensitivity has a 1/r dependence, where r represents the distance between a detected radiation event occurring in the object under consideration and the detection point on the detector. That is to say, the detector is generally more sensitive to relatively close objects and less sensitive to far away objects.

Reconstruction of linear projection data obtained using conventional Anger cameras usually incorporates back-projection using a form of the inverse Radon transform $R^{-1}$. Reconstruction of the planar projection data obtained from a slat-type camera is complicated in two respects. First, the integrations are planar integrations rather than line intregrals. Second, the 1/r term which occurs in projection data obtained by a slat detector reduces the spatial symmetry of the projection data. The reduced symmetry prevents the use of mathematical methods which are typically employed to implement the Radon transform R and its inverse $R^{-1}$.

Most previous reconstruction methods for projection data acquired by a slat detector merely disregard or ignore the 1/r weighting factor in solving the reconstruction problem. This approximation results in degradation of the reconstructed image. This type of image degradation could be reduced or even eliminated by a new or improved reconstruction algorithm which accounts for the 1/r dependence.

The present invention contemplates a new and improved reconstruction technique which overcomes the above-referenced problems and others.

SUMMARY OF THE INVENTION

In accordance with one aspect of the present invention, a nuclear medical imaging apparatus is disclosed. An object is received in a receiving region. A radiation detector has a side facing the receiving region. The detector includes a collimator fabricated from radiation attenuative material arranged on the detector side facing the receiving region. The collimator includes a plurality of spaced apart slats. The detector also includes an essentially linear array of detecting elements, the detecting elements being disposed between the slats on the detector side facing the receiving region. The imaging apparatus further includes an image reconstruction processor which converts the projection data from the detector into an image representation. The image reconstruction processor includes a memory, a preconditioning operator P, a projection operator S, and an iterative loop operator which applies the preconditioning operator P and the projection operator S to the memory contents to calculate updated memory contents. Preferably, the preconditioning operator P applies an inverse Radon transform operator $R^{-1}$. In one embodiment, the memory stores projection data, and the iterative loop operator applies the preconditioning operator P to the projection data stored in the memory, and then applies the projection operator S to produce a second set of projection data. The projection operator preferably incorporates a plurality of Radon transforms R, each Radon transform being applied to an image weighted by a weighting factor selected such that the projection operator approximates the projection transform physically implemented by the radiation detector, the approximating including at least approximating a 1/r dependence of the projection data generated by the radiation detector.

In accordance with another aspect of the present invention, a diagnostic imaging system is disclosed. A scanner generates projection data that is weighted inversely with distance in a projection direction. A backprojector backprojects the generated projection data into an image memory without compensating for the inverse weighting with distance to reconstruct an artifacted image representation. A forward projector forward projects the artifacted image to generate reprojected data. A correction circuit (i) compares the generated projection data and the reprojection data, and (ii) generates a correction factor in accordance with a deviation between the generated projection data and the reprojection data. The scanner preferably includes a one-dimensional array of radiation detectors, a collimator which collimates received radiation into planes, and a rotor for rotating radiation planes around an axis perpendicular to a face of the detector array.

In accordance with another aspect of the present invention, an image reconstruction process for generating a final image from measured projection data acquired by a slat detector is disclosed. The measured projection data is preconditioned using a preconditioning operator P to obtain an image. The image is iteratively improved to obtain a final image. The iterative process includes projecting the image with a projection operator S to generate reprojected data, comparing the reprojected data with the measured projection to generate correction data, and backprojecting one of the correction data, the reprojection data corrected with the correction data, and the projection data corrected with the correction data, using the preconditioning operator P to obtain an improved image. Preferably, the preconditioning operator P incorporates an inverse Radon transform $R^{-1}$.

In accordance with yet another aspect of the present invention, a diagnostic imaging process is disclosed. Projection data is generated which is weighted inversely with distance in a projection direction. The projection data is backprojected into an image representation without compensating for the inverse weighting to reconstruct a flawed image representation. The flawed image representation is forward projected to form reprojected data. The reprojected data is compared with the projection data. A correction is generated from a deviation between the reprojection data and the projection data. A backprojecting of one of: (i) the correction data into the flawed image representation; and (ii) the correction data combined with one of the projection and reprojection data is performed to generate a less flawed image representation. Steps starting with the forward projecting are iteratively repeated until the comparing step meets a preselected closeness criteria. Preferably, the backprojecting step uses an inverse Radon transform. The projection data generating step preferably includes: introducing a radiation source into a subject; collimating radiation from the source into planes; detecting the radiation in each plane; and rotating the collimation planes around a first axis parallel to at least one of the planes. Additionally, the data generating step may include rotating the collimation planes about a second axis through the subject and transverse to the first axis.

One advantage of the present invention is that it corrects for the 1/r dependence of the data.

Another advantage of the present invention is that it properly reconstructs data obtained from slat cameras.

Another advantage of the present invention is that it efficiently transforms the measured projection data into image space without neglecting the 1/r dependence of the slat detector projection data.

Yet another advantage of the present invention is that it utilizes the Radon transform R, which is often implemented in reconstruction algorithms for SPECT, PET, and other nuclear imaging methods, as a preconditioner.

Still further advantages and benefits of the present invention will become apparent to those of ordinary skill in the art upon reading and understanding the following detailed description.

BRIEF DESCRIPTION OF THE DRAWINGS

The invention may take form in various components and arrangements of components, and in various steps and arrangements of steps. The drawings are only for the purposes of illustrating preferred embodiments and are not to be construed as limiting the invention.

DETAILED DESCRIPTION OF THE PREFERRED EMBODIMENTS

Figure 1:
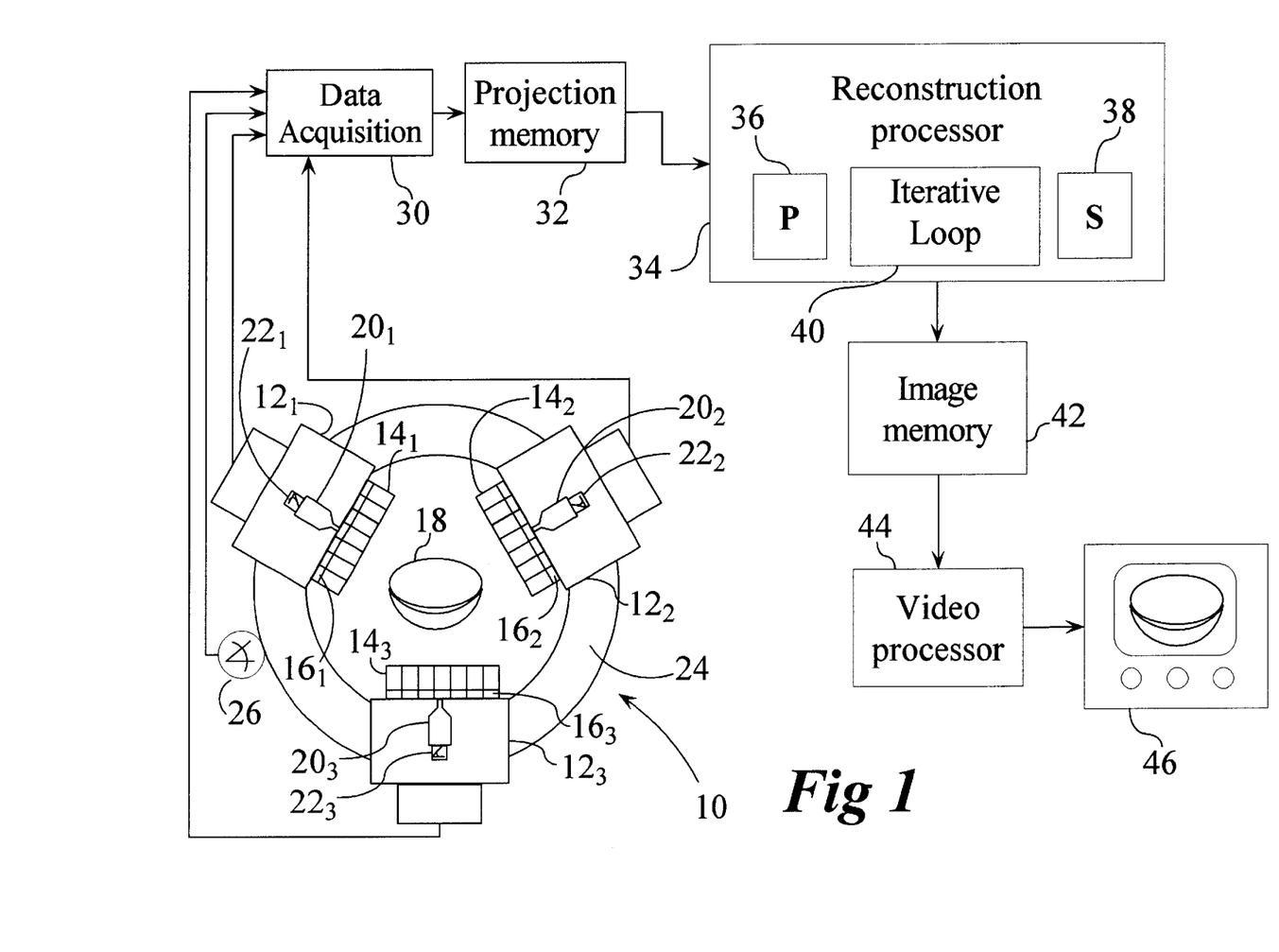
FIG. 1 is a diagram of a nuclear imaging system in accordance with the invention.

With reference to FIG. 1, a nuclear camera system 10 includes a plurality of slat-type detector heads 12, in the preferred embodiment three slat detector heads $12_1$, $12_2$, and $12_3$. Of course, other numbers of detector heads can also be utilized. Each of the detector heads includes a slat-type collimator $14_1$, $14_2$, and $14_3$ and a linear array of detectors $16_1$, $16_2$, and $16_3$. The collimators collimate incoming radiation from a subject 18 to parallel planes with an embedded 1/r dependence. Each camera detector-collimator unit is rotatable by a motor $20_1$, $20_2$ and $20_3$ about an axis perpendicular to the detector face and approximately centered thereon. Angular orientation monitors $22_1$, $22_2$, and $22_3$ track the angular orientation of the respective collimator/detector units.

A rotating gantry 24 rotates all three detector heads about the subject 18. An angular orientation monitor 26 determines the angular orientation of each of the heads at each angular data collection position. Each of the detector heads records radiation events in terms of which detector element received the radiation, angle of the collimator-detector unit within the head, and angle of the head around the subject.

A data acquisition system 30 receives the projection data along with the corresponding positional and angular parameters. This data is stored in a projection memory 32. The projection data is processed by reconstruction processor 34 which reconstructs an image from the projection data. The reconstruction processor includes at least a preconditioning processor 36 denoted by P and a projection processor 38 denoted by S which are used in conjunction with an iterative loop processor 40 to perform the reconstruction. The reconstructed image is preferably stored in an image memory 42 from which it is retrieved by a video processor 44 and displayed on a video monitor 46. Of course other output devices, such as a color printer, projector display, CCD display, active matrix display, or the like may also be used.

Figure 2A:
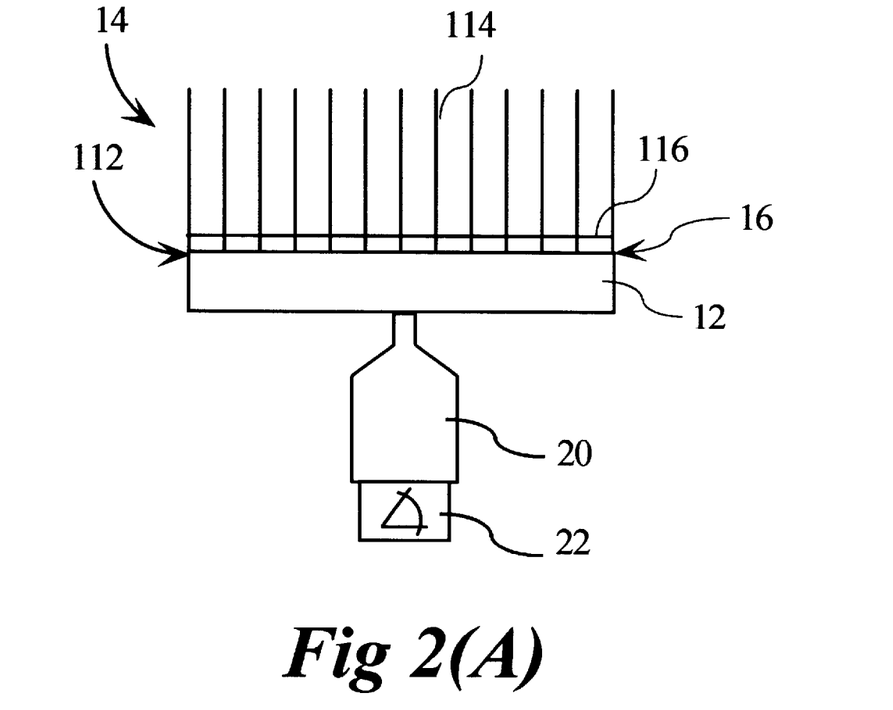
FIG. 2(A) is a side view of a slate detector in accordance with the present invention.
Figure 2B:
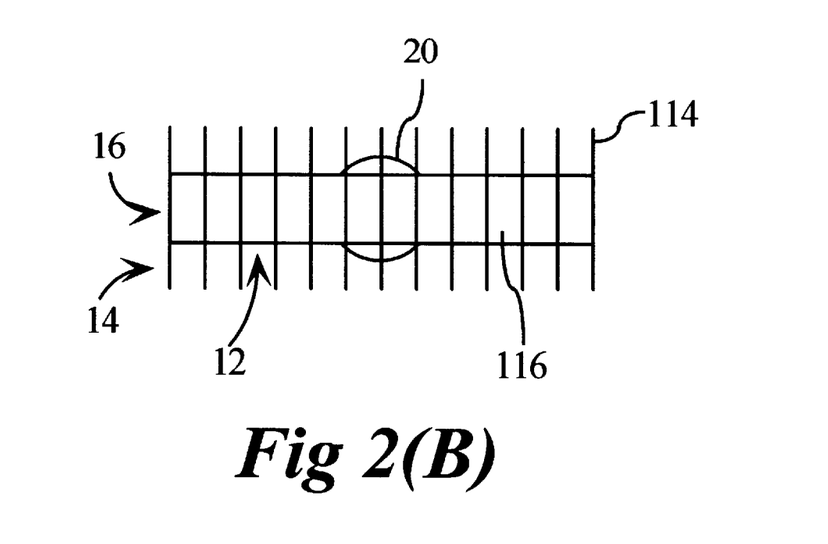
FIG. 2(B) is a top view of the slat detector of FIG. 2(A)

With reference to FIG. 2(A) and FIG. 2(B), each collimator 14 includes a plurality of collimator slats 114. The collimator slats are preferably perpendicular to a face of detector array 16, although uniformly or non-uniformly tilted slats are also contemplated. A plurality of detector elements 116 are located on the detector face 112 in the gaps between the slats. Detector elements 116 may be discrete detectors, or may be regions of a large area detector which are isolated by the slats.

Referring back to FIG. 1, the reconstruction processor 34 accepts projection data from projection memory 32 and calculates an image which is subsequently stored in image memory 42. The reconstruction processor includes a pre-conditioning processor 36 denoted by P and a projection processor 38 denoted by S which are used in conjunction with an iterative loop processor 40 to perform the reconstruction.

The reconstruction processor solves the equation $Sf(\theta, s) = g(\theta, s)$. If a preconditioner P is applied, this may be written as:

$$PSf(\theta,s) = Pg(\theta,s) \quad (1)$$

or equivalently, $$SPh = g, Ph = f \quad (2)$$

where $g(\theta, s)$ is the measured projection data, $f(\theta, s)$ is the image to be reconstructed, S is the slat detector projection operator 38, P is a preconditioner operator 36, and h is an intermediate variable. From equation (1) it is clear that the forward projection operator S acts to project the image f. S is therefore the mathematical equivalent of the projection transform physically implemented by the radiation detection system 10 and associated data acquisition system 30. To calculate the reconstructed image f, the reconstruction processor effectively implements a backprojection operator $S^{-1}$. Alternatively, equation (2) indicates that if $(PS)^{-1}$ and P are implementable, then h and subsequently f may be calculated from the measured projection data set g. Furthermore, if PS is close to unity, a Neumann series representation may be employed, $$(PS)^{-1} = \sum_k (I - PS)^k \quad (3)$$

where I is the identity operator. Thus, to implement the slat detector backprojection operator $S^{-1}$, the invention employs implementable expressions for the slat detector projection S and for a preconditioner P as described below, with the further restriction that PS be close to unity so that the Neumann series is appropriate. The preferred preconditioner P, as detailed next, is the inverse Radon or filtered back-projection transform $R^{-1}$.

The imaged area is contained within an imaging volume which in the case of a slat detector is a spherical volume of radius R. The Radon transform R is defined by:

$$Rf = \int_{x \cdot \theta = s} f(x) dx \quad (4)$$

where f is the image contained within the imaging volume.

The slat detector projection is described by transform S as, $$Sf = \int_{x \cdot \theta = s} \frac{f(x)}{|x-a|} dx, \; a = s\theta + R_s \theta_{1,\perp} \quad (5)$$

using the parameterizations, $$\theta(\varphi, \psi) = \begin{pmatrix} \cos\varphi \sin\psi \\ \sin\varphi \sin\psi \\ \cos\psi \end{pmatrix} = \begin{pmatrix} \sin\psi \theta(\varphi) \\ \cos\psi \end{pmatrix} \quad (6)$$

$$\theta_{1,\perp}(\varphi, \psi) = \begin{pmatrix} -\sin\varphi \\ \cos\varphi \\ 0 \end{pmatrix} = \begin{pmatrix} \theta_\perp(\varphi) \\ 0 \end{pmatrix}$$

$$\theta_{2,\perp}(\varphi, \psi) = \begin{pmatrix} \cos\varphi \cos\psi \\ \sin\varphi \cos\psi \\ -\sin\psi \end{pmatrix} = \begin{pmatrix} \cos\psi \theta(\varphi) \\ -\sin\psi \end{pmatrix}$$

$$\theta(\varphi) = \begin{pmatrix} \cos\varphi \\ \sin\varphi \end{pmatrix}, \; \theta_\perp(\varphi) = \begin{pmatrix} -\sin\varphi \\ \cos\varphi \end{pmatrix} = \theta\left(\varphi + \frac{\Pi}{2}\right)$$

where $R_S$ is the distance from the detector to the object.

For the limit $R_S \to \infty$, the approximation $Rf(\theta, s) \sim R_S Sf(\theta, s)$ holds. This implies that a suitable preconditioning operator P is the filtered backprojection operator, i.e. the inverse filtered Radon transform $R^{-1}$. However, in applying the inverse Radon transform $R^{-1}$ to slat detector data a complication arises due to the reduced symmetry of the slat detector data versus conventional Anger camera data. For the Radon transform, the following symmetries apply, $$Rf(\varphi,\psi,s) = Rf(\varphi,\psi+\pi,-s) = Rf(\varphi+\pi,-\psi,s) = Rf(\varphi+\pi,\pi-\psi,-s) \quad (7).$$

Thus, the backprojection needs to be performed on the data for $\varphi$ and $\psi$ in the range $[0, \pi]$ only. For the slat detector projection transform S, since the weight depends on the value of $\varphi$, the symmetries are reduced to, $$Sf(\psi,\psi,s) = Sf(\psi,-\psi,-s) \quad (8)$$

without further relations, so non-redundant projection data occurs for $\varphi$ in the range $[0, 2\pi]$. Thus, when applying the inverse Radon transform $R^{-1}$ to projection data obtained by a slat detector, the projection data for $\varphi$ and $-\varphi$ are averaged to account for the lack of redundancy.

Turning next to the implementation of the slat detector projection operator S, it is shown that S can be implemented by applying a plurality of Radon transforms R, each Radon transform being applied to the image weighted by a weighting factor. The approach is therefore to develop a fast Radon transform, and then to extend this to implement the slat detector projection operator S.

The Radon transform R can be written as, $$Rf = \int_{x \cdot \theta = s} f(x) dx \quad (9)$$

$$= \int \int f(s\theta + u\theta_{1,\perp} + v\theta_{2,\perp}) du dv$$

$$= \int \int f \begin{pmatrix} s \cos\varphi \sin\psi - u \sin\varphi + v \cos\varphi \cos\psi \\ s \sin\varphi \sin\psi + u \cos\varphi + v \sin\varphi \cos\psi \\ s \cos\psi - v \sin\psi \end{pmatrix} du dv$$

$$= \int \int f \begin{pmatrix} (s \sin\psi + v \cos\psi) \theta(\varphi) + u\theta_\perp(\varphi) \\ s \cos\psi - v \sin\psi \end{pmatrix} du dv.$$

Defining (10)

$$g_\varphi(x_1, x_3) = \int_u f \begin{pmatrix} x_1 \theta(\varphi) + u\theta_\perp(\varphi) \\ x_3 \end{pmatrix} du$$

we have $$Rf(\theta,s) = \int g_\psi(s \sin \psi + v \cos \psi, s \cos \psi - v \sin \psi) dv \quad (11).$$

The resulting algorithm for the evaluation of Rf is: (1) tabulate $g_\varphi(x_1, x_3)$ for $\varphi$ in the range $[0, 2\pi]$ and $x_1, x_3$ satisfying $x_1^2+x_3^2 \leq R$; and (2) compute Rf from g. Using a step size of $O(1/N)$ for all variables, the computational effort is $O(N^4)$. Since the algorithm only requires us to compute line integrals in 2D, it is readily implemented.

To extend the fast Radon transform to a fast slat detector projection transform S, it is first recognized that the integrals carry an additional weight. Direct separation of the integrand is not possible, since the weight depends upon both u and v, as $$Sf(\theta, s) = \int_u \int_v \frac{f(s\theta + u\theta_{1,\perp} + v\theta_{2,\perp})}{\sqrt{(u-R_s)^2 + v^2}} du dv. \quad (12)$$

Assume that the weight can be approximated by a sum of the following form, $$w(u,v) = \frac{1}{\sqrt{(u-R_s)^2 + v^2}} \sim \sum_{v=0}^{M} A_v(u-R_s)B_v(v) \quad (13)$$

for arbitrary functions $A_v$ and $B_v$. Thus, w is now a sum of separable functions in u and v. Then, $$Sf(\theta, s) = \sum_{v=0}^{M} \int_v B_v(v) \int_u f(s\theta + u\theta_{1,\perp} + v\theta_{2,\perp}) A_v(u-R_s) du dv \quad (14)$$

and g is defined analogous to the Radon transform case, $$g_{v,\varphi}(x_1, x_3) = \int_u f\left(\frac{x_1\theta(\varphi) - u\theta_\perp(\varphi)}{x_3}\right) A_v(u-R_s) du \quad (15)$$

so that the slat detector transform S is given by, $$Sf(\theta, s) = \sum_{v=0}^{M} \int_v g_{v,\varphi}(s\sin\psi + v\cos\psi, s\cos\psi - v\sin\psi)B_v(v)dv. \quad (16)$$

Comparing equation (16) with equation (11), it will be observed that the Radon transform R and the slat detector projection transform S differ by the $B_v(v)$ weighting.

Referring back to equation (11), since $u\theta_{1,\perp}+v\theta_{2,\perp}$ is a circle of radius R and $R_S>R$, $R_S-u$ is positive and the weight $w(u,v)$ can be written as, $$w(u,v) = \frac{1}{R_s - u} \cdot \frac{1}{\sqrt{1+(v/(R_s-u))^2}}. \quad (17)$$

Taking the second fraction as a function of $v/(R_S-u)$, it can be approximated by a polynomial with coefficients $\alpha_v$. Weight w is then approximated in the desired form by $$w(u,v) = \sum_{v=0}^{M} \left(\alpha_v \left(\frac{1}{R_s - u}\right)^{v+1}\right)(v^v). \quad (18)$$

To find the proper polynomial, the size of the argument must be estimated. As $u^2+v^2 \leq R$, the argument is smaller than $(R^2-u^2)^{1/2}/(R_s-u)$ with u in the interval $[-R, R]$. Since $R_S>R$, the maximum $u_{max}$ of that function is located at $R^2/R_S$ with the maximum value $R/(R_S^2-R^2)^{1/2}$. For the typical choices $R_S=1.2$ and $R=1$, a maximum value of about 1.51 is obtained.

The polynomial chosen should give a minimal absolute error for u in the range $[0, u_{max}]$. For the values $R_S=1.2$ and $R=1$ it is preferably found by the Remez algorithm to be $$1.003815469+(-0.0627153542+(-0.3875254049+ \\ 0.1541203805 \cdot x) \cdot x) \cdot x \quad (19)$$

with a maximum error of 0.004.

Figure 3:
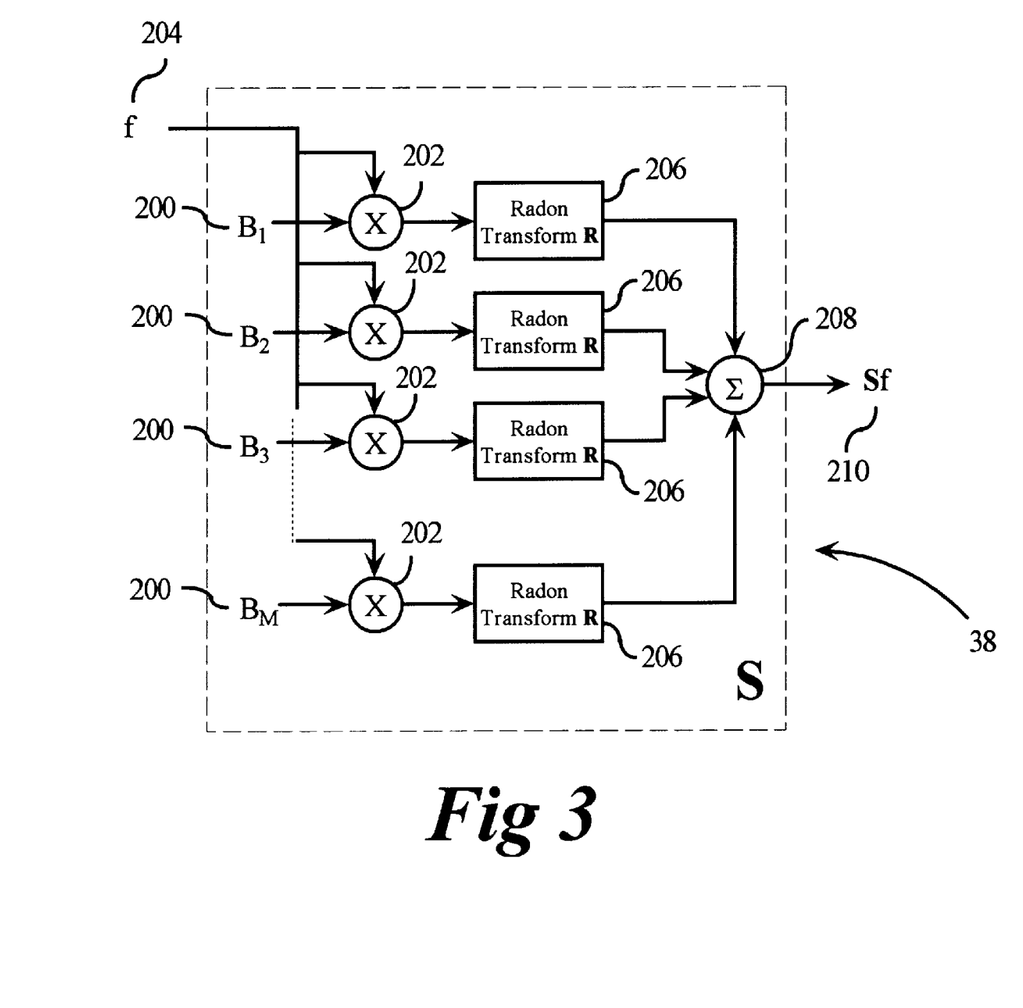
FIG. 3 is a block diagram of an implementation of the slat detector projection transform S in accordance with the invention.

The preferred implementation of the fast slat detector projection operator S (element 38 in FIG. 1) according to equation (16) is shown in FIG. 3. The $B_v$ weighting factors 200 are applied 202 to image f 204 and subsequently operated upon by Radon transforms 206. The summed result 208 yields the desired fast slat detector projection transform Sf 210.

Having identified a preferred preconditioner P as the inverse Radon transform $R^{-1}$ with the symmetry correction discussed previously, as well having obtained a fast slat detector projection transform S as exemplified by equation (16) and as illustrated in FIG. 3, a preferred algorithm implemented by reconstruction processor 34 will now be disclosed. Combining equation (1) with the Neumann series of equation (3) yields the iterative algorithm, $$f_{k+1}=f_k+p_{k+1},$$

where $$p_{k+1}=(I-PS)p_k \quad (20)$$

with the initial conditions, $$f_0=p_0, p_0=Pg \quad (21).$$

Figure 4:
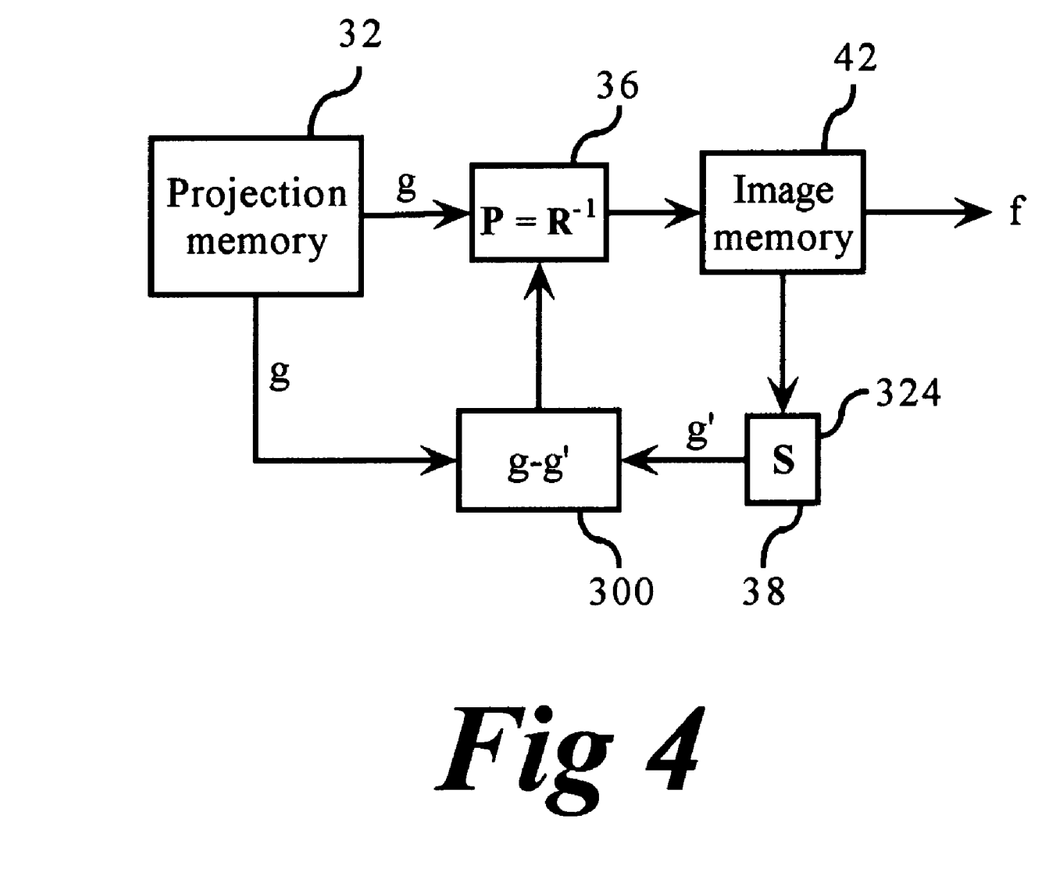
FIG. 4 is a block diagram of the reconstruction processor of FIG. 1.

With reference to FIG. 4, each view of projection data g from the projection memory 32 is backprojected 36 with the inverse Radon transform $R^{-1}$ into the image memory 42. Because the 1/r weighting error has been ignored, the reconstructed image is inaccurate. When the image is forward projected 38 along each of the original projection planes, the forward projected data g' deviates from the corresponding original projection data f. Corresponding forward projected and original projection data are compared 300 to determine a correction factor, e.g. subtracted. The set of correction factors are backprojected 36 into the image memory 42. With each iteration, the deviation becomes smaller as the reconstructed image converges on the precise reconstruction. Once the comparison 300 determines that the corrections are sufficiently small, the iterative correction process is terminated.

A second preferred algorithm is derived by combining equations (2) and (3) to yield:

$$f_{k+1}=Ph_{k+1},$$

where $$h_{k+1}=h_k+p_{k+1},$$

and $$p_{k+1}=(I-SP)p_k \quad (22)$$

with the starting conditions, $$f_0=Ph_0, h_0=p_0, p_0=g. \quad (23)$$

Figure 5:
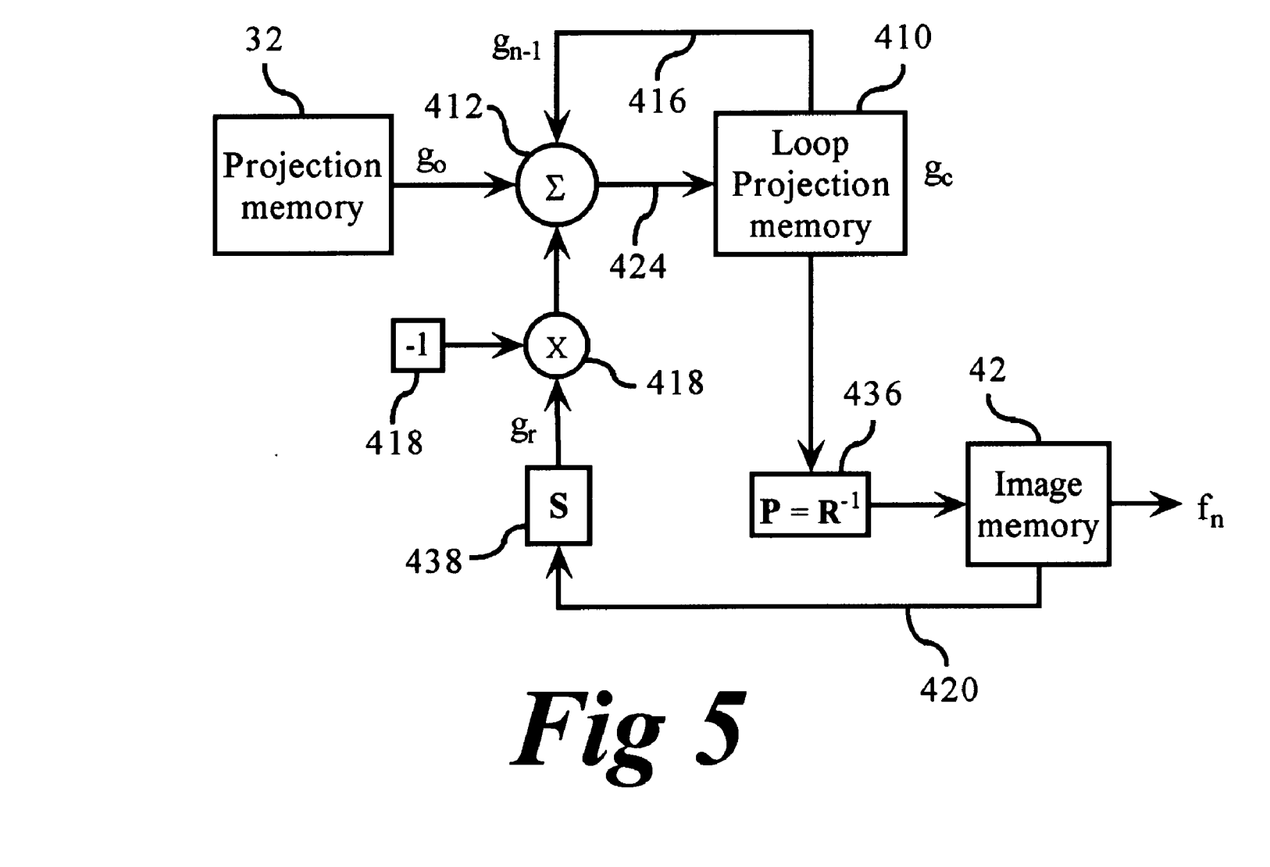
FIG. 5 is an alternate embodiment of the reconstruction processor.

The reconstruction processor algorithm of equations (22) and (23) is illustrated in FIG. 5. Measured slat detector projection data g stored in projection memory 32 of the nuclear imaging system (FIG. 1) is directly input into the initially zeroed loop projection memory 410 during the zeroeth iteration, in accordance with equation (23). Each loop iteration thereafter adds 412 an improved correction to the loop projection memory 410. The correction is formed as $h_{k+1}$ in accordance with equation (22) combining the difference between the original data $g_o$ and re-projected data $g_r$ with the last iteration corrected data $g_c$. In the zeroeth iteration the original projection data $g_o$ is moved into a loop projection memory 410. The projection data $g_o$ is backprojected 436 into the image memory 42. The image is re-projected 438 and its negative determined 418. The previous iteration of projection data $g_c$ is combined with the difference between the original projection data $g_o$ and the most recent iteration re-projected data $g_r$ to update the corrected projection data set. The updated projection data set $g_c$ is backprojected 436 using the inverse Radon transform $R^{-1}$ to generate a corrected image by subtracting 418 from the projection of the previous iteration 416 the projection formed by first backprojecting the loop projection memory using preconditioner 436, which once again is preferably an inverse Radon transform $R^{-1}$, and then re-projecting 438 the obtained image 420 using the slat detector projection operator S. The loop projection memory is updated 424. When the loop converges to a solution, the final image may be extracted from image memory 42 for further processing in accordance with FIG. 1.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A nuclear medical imaging apparatus comprising:
    a receiving region wherein an associated object is received;
    a radiation detector having a side which faces the receiving region, the detector including,
        a collimator fabricated from radiation attenuative material arranged on the detector side facing the receiving region, the collimator including a plurality of spaced apart slats, and
        an essentially linear array of detecting elements, the detecting elements being disposed between the slats on the detector side facing the receiving region; and
    an image reconstruction processor which converts projection data acquired by the detector into an image representation, the image reconstruction processor including,
        a memory storing memory contents,
        an inverse Radon transform preconditioning operator P,
        a fast slat detector projection operator S that includes a weighted combination of a plurality of Radon transform operators, and
        an iterative loop operator that corrects a 1/r dependence of the projection data by applying the preconditioning operator P and the projection operator S to the memory contents to calculate updated memory contents.

2. The nuclear medical imaging apparatus as set forth in claim 1, wherein:
    the preconditioning operator applies an inverse Radon transform operator $R^{-1}$.

3. The nuclear medical imaging apparatus as set forth in claim 1, wherein:
    the iterative loop operator implements a Neumann series of the form $$(PS)^{-1} = \sum_k (I - PS)^k$$

where P is the preconditioning operator, S is the projection operator, and I is an identity operator.

4. The nuclear medical imaging apparatus as set forth in claim 1, wherein:
    the memory stores an image; and
    the iterative loop operator applies the projection operator S to the image stored in the memory, and subsequently applies the preconditioning operator P to produce a second image.

5. The nuclear medical imaging apparatus as set forth in claim 1, wherein:
    the memory stores projection data; and
    the iterative loop operator applies the preconditioning operator P to the projection data stored in the memory, and then applies the projection operator S to produce a second set of projection data.

6. The nuclear medical imaging apparatus as set forth in claim 1, wherein each of the plurality of Radon transform operators is applied to an image weighted by a weighting factor.

7. The nuclear medical imaging apparatus as set forth in claim 6, wherein:
    the weighting factors are selected such that the projection operator approximates a projection transform physically implemented by the radiation detector, the approximating including at least approximating a 1/r dependence of the projection data generated by the radiation detector.

8. The nuclear medical imaging apparatus as set forth in claim 1, wherein:
    the iterative loop operator iteratively corrects for a 1/r dependence of the projection data.

9. The nuclear medical imaging apparatus as set forth in claim 1, wherein:
    the slats are perpendicular to the detector face.

10. A diagnostic imaging system comprising:
    a scanner which generates projection data that is weighted inversely with distance in a projection direction;
    a backprojector which backprojects the generated projection data into an image memory without compensating for the inverse weighting with distance to reconstruct an artifacted image representation;
    a forward projector which forward projects the artifacted image to generate reprojected data, the forward projecting including an inverse distance weighting; and
    a correction circuit which (i) compares the generated projection data and the reprojection data and (ii) generates a correction factor in accordance with a deviation between the generated projection data and the reprojection data.

11. The diagnostic imaging system as set forth in claim 10 wherein the scanner includes:
    a one-dimensional array of radiation detectors;
    a collimator which collimates received radiation into planes; and
    a rotor for rotating radiation planes around an axis perpendicular to a face of the detector array.

12. An image reconstruction process for generating a final image from measured slat collimated projection data acquired by a slat detector, the process comprising:

preconditioning the measured slat collimated projection data using a preconditioning operator P that includes an inverse Radon transform to obtain an image; and iteratively improving the image to obtain a final image, the iterative process including,
projecting the image with a slat collimated projection operator S to generate reprojected data, comparing the reprojected data with the measured projection data to generate correction data, and backprojecting one of the correction data, the reprojection data corrected with the correction data, and the projection data corrected with the correction data, using the preconditioning operator P to obtain an improved image.

13. An image reconstruction process for generating a final image from measured projection data acquired by a slat detector, the process comprising:

preconditioning the measured projection data using a preconditioning operator P to obtain an image; and iteratively improving the image to obtain a final image, the iterative process including projecting the image with a projection operator S to generate reprojected data, comparing the reprojected data with the measured projection to generate correction data, and backprojecting using the preconditioning operator P one of the correction data, the reprojection data corrected with the correction data, and the projection data corrected with the correction data to obtain an improved image, the iterative process implementing the iterative calculation, $$f_{k-1} = f_k + p_{k+1}$$

where $$p_{k+1} = (I-PS)p_k$$

with the initial conditions $$p_o = p_g, f_o = P_o$$

where g is the measured projection data, k is an iteration index, $f_k$ is an image at iteration k, and $(PS)p_k$ is the second image.

14. The image reconstruction process as set forth in claim 13, wherein:
the projection operator S is, $$Sf(\theta, s) = \sum_{\nu=0}^{M} \int_{\nu} g_{\nu,\varphi}(s \sin\psi + \nu \cos\psi, s \cos\psi - \nu \sin\psi) B_\nu(\nu) d\nu$$

where $B_\nu$ are weighting factors, and the remaining parameters are related to the Radon transform according to $$Rf(\theta,s) = \int g_\varphi(s \sin \phi + \nu \cos \psi, s \cos \psi - \nu \sin \psi) d\nu$$

15. A diagnostic imaging process comprising:
(a) generating projection data that is weighted inversely with distance in a projection direction;
(b) backprojecting the projection data into an image representation without compensating for the inverse weighting to reconstruct a flawed image representation;
(c) forward projecting reprojected data from the flawed image representation using a plurality of additively combined Radon transforms;
(d) comparing the reprojected data with the projection data;
(e) generating correction data from a deviation between the reprojection data and the projection data;
(f) backprojecting one of:
  (i) the correction data into the flawed image representation; and
  (ii) the correction data combined with one of the projection and reprojection data
to generate a less flawed image representation; and
(g) iteratively repeating steps (c)–(f) until the comparing step (d) meets a preselected closeness criteria.

16. The imaging process as set forth in claim 15, wherein:
the backprojecting step (b) uses an inverse Radon transform.

17. A diagnostic imaging process comprising:
generating projection data that is weighted inversely with distance in a projection direction;
first backprojecting the projection data into an image representation without compensating for the inverse weighting to reconstruct a flawed image representation;
forward projecting reprojected data from the flawed image representation using a projection operator S defined by:

$$Sf(\theta, s) = \sum_{\nu=0}^{M} \int_{\nu} g_{\nu,\varphi}(s \sin\psi + \nu \cos\psi, s \cos\psi - \nu \sin\psi) B_\nu(\nu) d\nu$$

where g is the generated projection data, $f_k$ is the flawed image representation, and $B_\nu$ are weighting factors, and the remaining parameters are related to the Radon transform R according to $$Rf(\theta,s) = \int g_{100}(s \sin \psi + \nu \cos \psi, s \cos \psi - \nu \sin \psi) d\nu$$

comparing the reprojected data with the projection data;
generating correction data from a deviation between the reprojection data and the projection data;
second backprojecting one of the correction data into a flawed image representation and the correction data combined with one of the projection and reprojection data to generate a less flawed image representation; and
iteratively repeating the forward projecting, comparing, generating, and second backprojecting until the comparing meets a preselected closeness criteria.

18. The imaging process as set forth in claim 15, wherein the projection data generating step includes:
introducing a radiation source into a subject;
collimating radiation from the source into planes;
detecting the radiation in each plane; and
rotating the collimation planes around a first axis parallel to at least one of the planes.

19. The imaging process as set forth in claim 18, wherein the projection data generating step further includes:
rotating the collimation planes about a second axis through the subject and transverse to the first axis.

* * * * *